Figure 1:
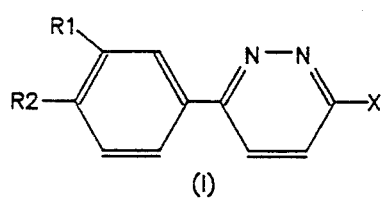
Figure 2:
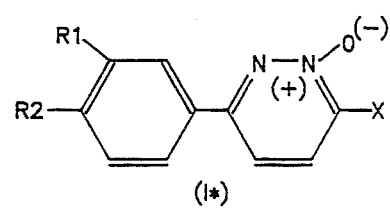
Figure 3:
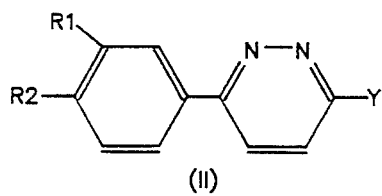
Figure 4:
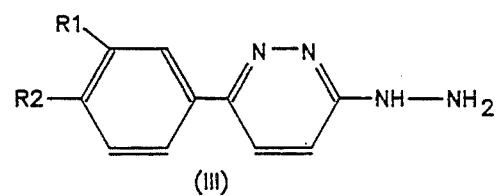
Figure 5:
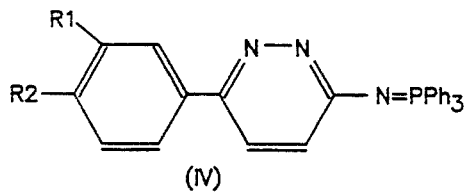
Figure 6:
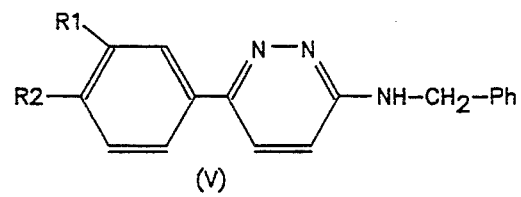

United States Patent [19]

Amschler et al.

[11] Patent Number: 5,449,676
[45] Date of Patent: Sep. 12, 1995

[54] PYRIDAZINES

[75] Inventors: Hermann Amschler, Radolfzell; Christian Schudt, Konstanz, both of Germany

[73] Assignee: BYK Gulden Lomberg Chemische Fabrik GmbH, Konstanz, Germany

[21] Appl. No.: 137,200

[22] PCT Filed: Apr. 21, 1992

[86] PCT No.: PCT/EP92/00872
§ 371 Date: Mar. 28, 1994
§ 102(e) Date: Mar. 28, 1994

[87] PCT Pub. No.: WO92/19602
PCT Pub. Date: Nov. 12, 1992

[30] Foreign Application Priority Data

Apr. 26, 1991 [CH] Switzerland ............ 01 255/91
Apr. 26, 1991 [CH] Switzerland ............ 01 256/91
Jul. 5, 1991 [CH] Switzerland ............ 01 997/91

[51] Int. Cl.⁶ .................... A61K 31/50; C07D 237/20
[52] U.S. Cl. ............................. 514/247; 544/224
[58] Field of Search ................ 544/224; 514/247

[56] References Cited

U.S. PATENT DOCUMENTS 4,665,074  5/1987  Amschler ............... 514/247
4,707,481 11/1987  Amschler et al. ....... 514/247
4,791,110 12/1988  Arnold et al. .......... 514/247

FOREIGN PATENT DOCUMENTS 393500 10/1990 European Pat. Off. .
06719 11/1986 WIPO .

Primary Examiner—Emily Bernhardt
Attorney, Agent, or Firm—Jacobson, Price, Holman & Stern

[57] ABSTRACT

Compounds of formula (I)

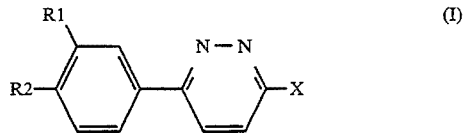

in which R1, R2 and X have the meanings given in the specification, and their salts and N oxides are new agents for the treatment of bronchial conditions and dermatitis.

8 Claims, 1 Drawing Sheet (I)

(I*)

(II)

(III)

(IV)

(V)

PYRIDAZINES

This application is a 371 of PCT/EP92/00872 filed Apr. 21, 1992.

TECHNICAL FIELD

The invention relates to 3-amino-6-arylpyridazines, processes for their preparation, their use and pharmaceuticals containing them. The compounds according to the invention are used in the pharmaceutical industry for the production of medicaments.

PRIOR ART

The described 3-amino-6-arylpyridazines are novel.

DESCRIPTION OF THE INVENTION

It has been found that the novel compounds described in detail below have advantageous pharmacological properties by which they differ from known compounds in a surprising and particularly advantageous manner.

The invention relates to 3-amino-6-arylpyridazines of the general formula I (see attached sheet of formulae), in which one of the substituents R1 and R2 denotes methoxy, difluoromethoxy or ethoxy and the other denotes 1–5C-alkoxy, 4–7C-cycloalkoxy, 3–7C-cycloalkylmethoxy, 3–5C-alkenyloxy or 1–4C-polyfluoroalkoxy, X denotes amino, and their salts with acids and their N-oxides.

1–5C-Alkoxy is straight-chain or branched. Examples of 1–5C-alkoxy radicals which may be mentioned are the methoxy, ethoxy, n-propoxy, isopropoxy, n-butoxy, isobutoxy, sec.-butoxy, tert.-butoxy, n-pentyloxy, isopentyloxy and 2,2-dimethylpropoxy radical. 3–4C-alkoxy is preferred.

4–7C-Cycloalkoxy represents, for example, cyclobutyloxy, cyclopentyloxy, cyclohexyloxy and cycloheptyloxy, of which cyclopentyloxy is preferred.

3–7C-Cycloalkylmethoxy represents, for example, cyclopropylmethoxy, cyclobutylmethoxy, cyclopentylmethoxy, cyclohexylmethoxy and cycloheptylmethoxy, of which cyclopropylmethoxy and cyclobutylmethoxy are preferred.

3–5C-Alkenyloxy is straight-chain or branched. The double bond of alkenyloxy does not start from the carbon atom which is bonded the oxygen atom. Examples of 3–5C-alkenyloxy radicals which may be mentioned are the buten-2-yloxy, the allyloxy and the methallyloxy radical.

1–5C-Alkoxy is preferred to 3–5C-alkenyloxy.

1–4C-Polyfluoroalkoxy means straight-chain or branched 1–4C-alkoxy in which at least two hydrogen atoms are replaced by fluorine. Straight-chain 1–3C-alkoxy in which at least two hydrogen atoms are replaced by fluorine is preferred. Preferred 1–4C-polyfluoroalkoxy groups are trifluoromethoxy, 1,1,2,2-tetrafluoroethoxy and, in particular, difluoromethoxy and 2,2,2-trifluoroethoxy.

Amino means the group $NH_2$.

Suitable and preferred salts for compounds of the formula I are all acid addition salts. Particular mention may be made of the pharmacologically acceptable salts of the inorganic and organic acids normally used in pharmaceutical technology. Pharmacologically unacceptable salts which may, for example, be the initial products of the process for the preparation of the compounds according to the invention on the industrial scale are converted into pharmacologically acceptable salts by processes known to the person skilled in the art. Suitable examples of these are acid addition salts which are soluble in water and insoluble in water, such as the hydrochloride, hydrobromide, hydroiodide, phosphate, nitrate, sulfate, acetate, citrate, gluconate, benzoate, hibenzate, fendizoate, butyrate, sulfosalicylate, maleate, laurate, malate, fumarate, succinate, oxalate, tartrate, amsonate, embonate, metembonate, stearate, tosylate, 3-hydroxy-2-naphthoate or mesylate.

The N-oxides of the compounds of the formula I can be described by the general formula I* (see sheet of formulae) in which R1, R2 and X have the abovementioned meanings.

The N-oxides of the 3-amino-6-arylpyridazines according to the invention can exist as tautomeric forms. One proton of the 3-amino group is able to migrate between this group and the oxygen in position 2 of the pyridazine ring. When only one tautomer is mentioned or depicted according to the invention, in each case the other tautomer is also to be understood.

One embodiment (embodiment a) of the invention comprises 3-amino-6-arylpyridazines of the general formula I in which
R1 denotes methoxy, difluoromethoxy or ethoxy,
R2 denotes 1–4C-alkoxy, 4–7C-cycloalkoxy, 3–6C-cycloalkylmethoxy, 3–4C-alkenyloxy or 1–2C-polyfluoroalkoxy and
X denotes amino,
and their salts with acids and their N-oxides.

Another embodiment (embodiment b) of the invention comprises 3-amino-6-arylpyridazines of the general formula I in which
R1 denotes 3–4C-alkoxy, 4–7C-cycloalkoxy, 3–6C-cycloalkylmethoxy, 3–4C-alkenyloxy or 1–2C-polyfluoroalkoxy,
R2 denotes methoxy, difluoromethoxy or ethoxy, and
X denotes amino,
and their salts with acids and their N-oxides.

Preferred compounds according to the invention are those of the formula I in which one of the substituents R1 and R2 denotes methoxy, difluoromethoxy or ethoxy and the other denotes 1–4C-alkoxy, 4–7C-cycloalkoxy, 3–6C-cycloalkylmethoxy or 1–2C-polyfluoroalkoxy, and X denotes amino, and their salts with acids and their N-oxides.

Preferred representatives of embodiment a are those in which R2 denotes 1–4C-alkoxy or 1–2C-polyfluoroalkoxy.

Preferred representatives of embodiment b are those in which R1 denotes 3–4C-alkoxy, 4–7C-cycloalkoxy, 3–6C-cycloalkylmethoxy or 1–2C-polyfluoroalkoxy.

Embodiment b is preferred to embodiment a.

Particularly preferred compounds according to the invention are those of the formula I in which R1 denotes 2–4C-alkoxy, cyclopentyloxy, cyclopropylmethoxy, cyclobutylmethoxy, difluoromethoxy or 2,2,2-trifluoroethoxy, R2 denotes methoxy, ethoxy or difluoromethoxy, and X denotes amino, and their pharmacologically acceptable salts with acids and their N-oxides.

The invention furthermore relates to a process for the preparation of the 3-amino-6-arylpyridazines of the general formula I in which R1, R2 and X have the abovementioned meanings, and their salts with acids and their N-oxides, wherein a) compounds of the formula II (see attached sheet of formulae) in which R1 and R2 have the abovementioned meaning, and Y is a leaving group which can undergo nucleophilic displacement, are reacted with ammonia or wherein b) 3-hydrazinopyridazine of the formula III (see attached sheet of formulae) in which R1 and R2 have the abovementioned meaning is catalytically hydrogenated, or wherein c) phosphazenes of the formula IV (see attached sheet of formulae) in which R1 and R2 have the abovementioned meaning are hydrolysed, or wherein d) benzyl compounds of the formula V (see attached sheet of formulae) in which R1 and R2 have the abovementioned meaning are catalytically hydrogenated, and wherein, if required, subsequently the compounds I obtained according to a), b), c) or d) are converted into their salts, or wherein, if required, subsequently the compounds I are liberated from resulting salts of the compounds I, or wherein, if required, subsequently the compounds I obtained according to a), b), c) or d) are converted into their N-oxides.

The process according to variant a) is carried out in a manner familiar to the person skilled in the art. Particularly suitable leaving groups Y which can undergo nucleophilic displacement are halogen atoms, especially chlorine and bromine. The reaction with ammonia is preferably carried out as described by E. A. Steck et al., J. Heterocycl. Chem. 12, 1009, 1975 in an alcohol such as ethanol, ethylene glycol or polyethylene glycol 400, preferably using excess ammonia at temperatures from 150° to 200° C., preferably at 180° to 200° C., in an autoclave.

In the process according to variant b), the 3-hydrazinopyridazines of the formula III are hydrogenated in a manner known to the person skilled in the art. For example, the compounds III are hydrogenated in an alcohol, preferably methanol, with an addition of a hydrogenation catalyst such as Raney nickel or palladium/carbon at temperatures between 20° and 65° C., preferably at room temperature. Alternatively, the compounds III can be subjected to catalytic transfer hydrogenolysis as described, for example, by G. Brieger and T. J. Nestrick in Chem. Rev. 74, 567 (1974). According to this, the compounds III are initially converted into their salts with a mineral acid such as hydrochloric or sulfuric acid, and subsequently hydrogenated in an alcohol such as, for example, methanol or ethanol with palladium/carbon and a hydrogen donor such as cyclohexene, cyclohexadiene, formic acid or ammonium formate at temperature from 20° to 80° C.

The hydrolysis of the phosphazenes IV according to process variant c) is carried out in a manner known per se, preferably in dilute mineral acids such as hydrochloric acid or sulfuric acid, or in aqueous organic acids such as acetic acid or formic acid.

The process according to process variant d) is likewise carried out in a manner known per se, with the debenzylation of the benzyl compounds V preferably taking place under the conditions of catalytic transfer hydrogenolysis, for which purpose the compounds V are debenzylated, for example, in a mixture of glacial acetic acid/concentrated hydrochloric acid and cyclohexene in the presence of palladium/carbon as catalyst.

Acid addition salts are obtained by dissolving the free base in a suitable solvent, for example in a chlorinated hydrocarbon such as methylene chloride or chloroform, or a low molecular weight aliphatic alcohol (ethanol, isopropanol), which contains the desired acid, or to which the desired acid is subsequently added.

The salts are obtained by filtration, reprecipitation, precipitation using a nonsolvent for the addition salt or by evaporation of the solvent. Resulting salts can be converted into the free bases by alkalinization, for example with aqueous ammonia solution, and the bases in turn can be converted into acid addition salts. It is possible in this way to convert pharmacologically unacceptable acid addition salts into pharmacologically acceptable acid addition salts.

The N-oxidation is carried out in a manner familiar to the person skilled in the art as described, for example, by Eiji Ochiai in "Aromatic Amine Oxides", page 22–26, Elsevier Publishing Company, Amsterdam London New York, 1967. Suitable oxidizing agents are all reagents commonly used for N-oxidation, especially hydrogen peroxide or (where appropriate prepared in situ) organic and inorganic peroxy compounds such as, for example, peroxyacetic acid, trifluoroperoxyacetic acid, 3,5-dinitroperoxybenzoic acid, peroxymaleic acid, m-chloroperoxybenzoic acid or potassium permanganate.

The compounds of the formula II are known or can be prepared by known processes as described, for example, in EP-A 393500.

The 3-hydrazinopyridazines of the formula III are obtained, for example, by reacting compounds of the formula II as described by C. G. Wermuth et al., J. Med. Chem., 30, 239, 1987, with hydrazine hydrate at 100° C., preferably in an inert solvent, for example in an alcohol such as 1-butanol, or without solvent.

The phosphazenes of the formula IV are likewise obtained starting from compounds of the formula II, which are initially converted as described by Th. Kappe et al., Synthesis 1989, 666, by the technique of phase-transfer catalysis (see J. Dockx, Synthesis 1973, 441) into tetrazolo[1,5-b]pyridazines.

For this purpose, the compounds II are reacted, for example in a hydrocarbon such as, for example, toluene or xylene, or in an ether such as, for example, dioxane, or in a ketone such as, for example, 2-methyl-4-pentanone (isobutyl methyl ketone), or in a N,N-di-substituted amide such as, for example, dimethylformamide or N-methylpyrrolidone, under anhydrous conditions, preferably in the presence of 0.1 to 1.0 mole of the phase-transfer catalyst at temperatures from 50° to 200° C., in particular from 80° to 150° C., preferably at the boiling point of the solvent, with at least 1 mole of alkali metal azide. Suitable phase-transfer catalysts are those customary for nucleophilic displacements, in particular for halogen replacement. Suitable examples are group ethers, quaternary phosphonium salts and, in particular, quaternary ammonium salts such as, for examples, tetrabutylammonium chloride.

The resulting tetrazolo[1,5-b]pyridazines are subsequently converted into the phosphazenes IV by heating with at least 1 mole of triphenylphosphine in an inert solvent such as benzene, toluene, xylene or chlorobenzene at 80° to 150° C., in particular at 80° to 135° C., preferably at the boiling point of the solvent.

The compounds of the formula V are prepared from the corresponding compounds II by heating with benzylamine, preferably without solvent at temperatures from 140° to 200° C., preferably at 180° to 190° C.

Employed for the preparation of the compounds of embodiments a and b are corresponding starting compounds of the general formula II, III, IV and V, in which R1 and R2 have the abovementioned meanings in each case.

The following examples serve to illustrate the invention in detail. M.p. denotes melting point, b.p. denotes boiling point.

EXAMPLES

1.
3-Amino-6-(3-methoxy-4-propoxyphenyl)pyridazine 10 g (35.9 mmol) of 3-chloro-6-(3-methoxy-4-propoxyphenyl)pyridazine are heated in 50 ml of ethylene glycol which has been saturated with ammonia at 0° C. in an autoclave at 220° C. for 6 hours. After cooling, the reaction mixture is diluted with 500 ml of water, and the precipitate which forms is filtered off with suction. The crude product is dried and then purified by column chromatography on silica gel with chloroform as eluent. 7.6 g (81.7%) of the title compound of m.p. 147° C. are obtained.

2.
3-Amino-6-[4-methoxy-3-(2-methylpropoxy)phenyl]-pyridazine 7.0 g (24 mmol) of 3-chloro-6-[4-methoxy-3-(2-methylpropoxy)phenyl]pyridazine are reacted as described in Example 1 in 40 ml of ammonia-saturated ethylene glycol. The crude product obtained by precipitation with water is dissolved in chloroform, the solution is dried with potassium carbonate, and the product is precipitated with petroleum ether (b.p. 50°–70° C.). 3.5 g (53.8%) of the title compound of m.p. 187° C. are obtained.

The following are obtained analogously using corresponding 3-chloro-6-arylpyridazines:
3-amino-6-[4-methoxy-3-(1-methylethoxy)phenyl]-pyridazine m.p. 184° C. (81.7%)
3-amino-6-[3-methoxy-4-(2-methylpropoxy)phenyl]-pyridazine m.p. 140° C. (76.1%)
3-amino-6-[3-methoxy-4-(1-methylethoxy)phenyl]-pyridazine m.p. 153° C. (89.8%)
3-amino-6-(3-cyclopentyloxy-4-methoxyphenyl)pyridazine m.p. 207° C. (99.2%)
3-amino-6-(3-cyclohexyloxy-4-methoxyphenyl)pyridazine m.p. 199° C. (72.3%)
3-amino-6-(3-cycloheptyloxy-4-methoxyphenyl)pyridazine m.p. 142° C. (88.1%)
3-amino-6-[4-ethoxy-3-(2-methylpropoxy)phenyl]-pyridazine m.p. 144° C. (91.5%)
3-amino-6-(4-difluoromethoxy-3-ethoxyphenyl)pyridazine m.p. 141° C. (98.4%)
3-amino-6-(4-difluoromethoxy-3-methoxyphenyl)-pyridazine m.p. 187°–188° C. (86.5%)
3-amino-6-(3-difluoromethoxy-4-ethoxyphenyl)pyridazine m.p. 170° C. (96.7%)
3-amino-6-(3-cyclobutylmethoxy-4-methoxyphenyl)-pyridazine m.p. 197° C. (34.5%)
3-amino-6-(3-cyclopentyloxy-4-difluoromethoxyphenyl)pyridazine m.p. 111°–2° C. (91.1%)
3-amino-6-[4-difluoromethoxy-3-(1-methylethoxy)-phenyl]pyridazine m.p. 153° C. (100.0%)
3-amino-6-[4-difluoromethoxy-3-(2,2,2-trifluoroethoxy)phenyl]pyridazine m.p. 96° C. (88.3%)
3-amino-6-[4-difluoromethoxy-3-(2-methylpropoxy)-phenyl]pyridazine m.p. 120°–1° C. (88.0%)
3-amino-6-(3-cyclopropylmethoxy-4-difluoromethoxyphenyl)pyridazine m.p. 106° C. (64.1%).

3.
3-Amino-6-(3-cyclopentyloxy-4-methoxyphenyl)-pyridazine a) 14 g (46 mmol) of 3-chloro-6-(3-cyclopentyloxy-4-methoxyphenyl)pyridazine are heated in 74 g (0.69 mol) of benzylamine at 200° C. for 3 hours. The mixture is subsequently poured onto ice and extracted with dichloromethane, and the organic phase is dried with potassium carbonate and then concentrated. Petroleum ether (b.p. 50°–70° C.) is added to the residue, and the resulting precipitate is filtered off with suction and crystallized from ethyl acetate/cyclohexane. 15.9 g (92.4%) of 3-benzylamino-6-(3-cyclopentyloxy-4-methoxyphenyl)pyridazine of m.p. 116° C. are obtained.

b) 15 g (40 mmol) of 3-benzylamino-6-(3-cyclopentyloxy-4-methoxyphenyl)pyridazine are heated to reflux in a mixture of 100 ml of glacial acetic acid, 6.5 ml of concentrated hydrochloric acid, 9.8 g (0.12 mol) of cyclohexene and 3 spatula tips of Pd/C (10 percent) for 4 hours. 9.8 g of cyclohexene and Pd/C are added once again, and boiling is continued for 16 hours. The catalyst is filtered off, the solution is diluted with 1 l of water and neutralized with concentrated ammonia, and the resulting precipitate is filtered off with suction. The product is purified by chromatography on silica gel with dichloromethane. 4.8 g (42.1%) of 3-amino-6-(3-cyclopentyloxy-4-methoxyphenyl)pyridazine of m.p. 207° C. are obtained.

4.
3-Amino-6-(4-difluoromethoxy-3-methoxyphenyl)-pyridazine a) 5 g (17 mmol) of 3-chloro-6-(4-difluoromethoxy-3-methoxyphenyl)pyridazine are heated in 30 ml of benzylamine at 180° C. for 1 hour. The mixture is stirred into 500 ml of saturated potassium carbonate solution, and the resulting precipitate is filtered off with suction, washed thoroughly with water, dried and recrystallized from ethyl acetate. 4.8 g (77.4%) of 3-benzylamino-6-(4-difluoromethoxy-3-methoxyphenyl)pyridazine of m.p. 136° C. are obtained.

b) 1.8 g (50.4 mmol) of 3-benzylamino-6-(4-difluoromethoxy-3-methoxyphenyl)pyridazine are dissolved in 30 ml of ethanol, 0.42 ml of concentrated hydrochloric acid is added, and the mixture is evaporated to dryness in a rotary evaporator. The hydrochloride which has formed is redissolved in 30 ml of ethanol, 0.95 g of ammonium formate and 0.5 g of palladium/carbon (10%) are added, and the mixture is boiled under reflux. The progress of the debenzylation is followed by thin-layer chromatography, and further ammonium formate and catalyst are added if necessary. After the reaction is complete, the catalyst is filtered off, and the solution is made alkaline with 2N sodium hydroxide solution and extracted with ethyl acetate. The organic phase is dried over calcined potassium carbonate, filtered with suction to remove desiccant and evaporated, and the residue is chromatographed on silica gel with ethyl acetate. Evaporation of the appropriate fractions results in 0.9 g (69.2%) of 3-amino-6-(4- difluoromethoxy-3-methoxyphenyl)pyridazine of m.p. 184° C.

5.
3-Amino-6-]4-methoxy-3-(1-methylethoxy)phenyl]-pyridazine a) 25 g (90 mmol) of 3-chloro-6-[4-methoxy-3-(1-methylethoxy)phenyl]pyridazine are boiled under reflux with 22.5 g (0.45 mol) of hydrazine hydrate in 200 ml of butanol for 12 hours. The reaction mixture is subsequently diluted to three to four times the volume with ice-water, and the precipitate is filtered off and recrystallized from isopropanol/cyclohexane. 18.9 g (76.8%) of 3-hydrazino-6-[4-methoxy-3-(1-methylethoxy)phenyl]pyridazine of m.p. 116° C. are obtained.

b) 10 g (36 mmol) of 3-hydrazino-6-[4-methoxy-3-(1-methylethoxy)phenyl]pyridazine are hydrogenated in 100 ml of methanol in the presence of 1 g of Raney nickel with hydrogen under atmospheric pressure at room temperature while stirring efficiently. Starting material is no longer detectable after 4 hours. The solution is filtered to remove catalyst and concentrated in vacuo, and the residue is crystallized from isopropanol/cyclohexane. 4.3 g (46%) of 3-amino-6-[4-methoxy-3-(1-methylethoxy)phenyl]pyridazine of m.p. 184° C. are obtained.

6. 3-Amino-6-(4-difluoromethoxy-3-methoxyphenyl)-pyridazine a) 20.0 g (69.8 mmol) of 3-chloro-6-(4-difluoromethoxy-3-methoxyphenyl)pyridazine are boiled under reflux in 100 ml of n-butanol with 17 ml (350 mmol) of hydrazine hydrate for 8 hours. The solution is cooled to about 80° C. and stirred with 100 ml of saturated sodium carbonate solution and 200 ml of water. The precipitate is filtered off with suction, washed with water and dried in vacuo. 18.4 g (93.4%) of 3-hydrazino-6-(4-difluoromethoxy-3-methoxyphenyl)pyridazine of m.p. 154° C. are obtained.

b) 5.0 g (18 mmol) of 3-hydrazino-6-(4-difluoromethoxy-3-methoxyphenyl)pyridazine are dissolved in 50 ml of ethanol and 2.3 ml (27 mmol) of concentrated hydrochloric acid, 1 g of palladium/carbon and 3.4 g (54 mmol) of ammonium formate are added, and the mixture is heated to 80° C. After evolution of gases has ceased, the mixture is stirred for a further 3 hours, filtered to remove the catalyst, and the solution is stirred in 1 l water and made alkaline with concentrated ammonia, and the resulting precipitate is collected on a suction funnel. The filter cake is thoroughly washed with water and then dried and chromatographed in a 95:5 mixture of dichloromethane/methanol on silica gel. The appropriate fractions are concentrated in vacuo. 3 g (63.6%) of 3-amino-6-(4-difluoromethoxy-3-methoxyphenyl)pyridazine of m.p. 184° C. are obtained.

7. 3-Amino-6-(4-difluoromethoxy-3-ethoxyphenyl)pyridazine 2-oxide 8.9 g (31.6 mmol) of 3-amino-6-(4-difluoromethoxy-3-ethoxyphenyl)pyridazine in 60 ml of glacial acetic acid are heated with 10.9 g (63.2 mmol) of m-chloroperoxybenzoic acid with stirring at 60° C. for 2 h. After cooling, the solution is stirred into 100 ml of water, the solution is exhaustively extracted with ethyl acetate, and the organic extract is dried over magnesium sulfate, concentrated in vacuo and chromatographed on neutral silica gel first with ethyl acetate and then with ethyl acetate/methanol 8:2. The appropriate fractions are concentrated, the residue is taken up in a little ethyl acetate, petroleum ether (b.p. 40°–70° C.) is added to incipient opalescence, and the product is crystallized by cooling. The crystals are filtered off with suction, washed with petroleum ether and dried at 80° C. in vacuo. 5.7 g (60.7%) of the title compound of m.p. 202°–3° C. are obtained.

8. 3-Amino-6-(4-difluoromethoxy-3-methoxyphenyl)-pyridazine 2-oxide 20.0 g (74.8 mmol) of 3-amino-6-(4-difluoromethoxy-3-methoxyphenyl)pyridazine are dissolved in 100 ml of glacial acetic acid and, while stirring, 30.6 ml (300 mmol) of 30% strength hydrogen peroxide are added, and the mixture is stirred at 80° C. for 2.5 h. The reaction solution is diluted with 1 kg of ice and 200 ml of concentrated ammonia solution, and the precipitate which has formed is collected on a suction funnel, washed first with water and then with ethanol and petroleum ether (b.p. 40°–70° C.) and dried at 75° C. in vacuo. 18.1 g (85.4%) of the title compound of m.p. 214° C. are obtained.

The following are obtained analogously using corresponding 3-amino-6-phenylpyridazines:
3-amino-6-(3-difluoromethoxy-4-ethoxyphenyl)pyridazine 2-oxide m.p. 188° C. (53.4%)
3-amino-6-[4-difluoromethoxy-3-(1-methylethoxy)-phenyl]pyridazine 2-oxide m.p. 207° C. (29.2%)
3-amino-6-[4-difluoromethoxy-3-(2-methylpropoxy)-phenyl]pyridazine 2-oxide m.p. 134°–35° C. (51.0%)
3-amino-6-(3-cyclopentyloxy-4-difluoromethoxyphenyl)pyridazine 2-oxide m.p. 167° C. (52.4%)
3-amino-6-[4-difluoromethoxy-3-(2,2,2-trifluoroethoxy)phenyl]pyridazine 2-oxide m.p. 222° C. (42.3%)
3-amino-6-(3-cyclopropylmethoxy-4-difluoromethoxyphenyl)pyridazine 2-oxide m.p. 159° C. (86.4%).

INDUSTRIAL APPLICABILITY

The 3-amino-6-arylpyridazines according to the invention and their salts and N-oxides have valuable pharmacological properties which make it possible to utilize them industrially. They are particularly distinguished by properties such that they appear suitable for the therapy of respiratory tract disorders of various etiologies. In particular, because of the antiinflammatory and bronchodilating activity of the compounds according to the invention, inflammatory and allergeninduced bronchial disorders can be treated. In addition, the compounds according to the invention are distinguished by a low toxicity, a high therapeutic index and the absence of substantial side effects.

The bronchodilating and antiinflammatory activity of the compounds according to the invention makes it possible to use them in human and veterinary medicine, in which case they are used for the treatment and prophylaxis of illnesses based on disorders of the bronchi. For example, acute and chronic obstructive respiratory tract disorders of various etiologies (bronchitis, allergic bronchitis, bronchial asthma) in humans and animals can be treated.

The invention therefore also relates to a method for the treatment of mammals, including humans, which are suffering from one of the abovementioned illnesses. The method comprises a therapeutically effective and pharmacologically acceptable amount of one or more of the compounds according to the invention being administered to the mammal with the illness.

The invention also relates to the compounds according to the invention for use for the treatment and/or prophylaxis of illnesses based on disorders of the bronchi.

The invention likewise relates to the use of the compounds according to the invention for the preparation of pharmaceuticals which are used for the treatment and/or prophylaxis of illnesses based on disorders of the bronchi.

The invention furthermore relates to pharmaceuticals for the treatment and/or prophylaxis of illnesses which are based on disorders of the bronchi and which contain one or more of the compounds according to the invention and/or their pharmacologically acceptable salts.

The pharmaceuticals according to the invention are prepared by processes known per se, reference being made to the statements in European Patent 163 965, for example, concerning the preparations, dosages, presentations etc.

The 3-amino-6-arylpyridazines according to the invention, and their salts and N-oxides, are furthermore suitable in an outstanding manner for the treatment of dermatoses.

Dermatoses which may be particularly mentioned are proliferative, inflammatory and allergic skin disorders. Thus, the compounds of the formula I can be used, for example, to prevent and treat the following skin disorders: psoriasis vulgaris, toxic and allergic contact dermatitis, atopic dermatitis, seborrhoeic dermatitis, follicular and extensive pyoderma, endogenous and exogenous acne, acne rosacea and other proliferative, inflammatory and allergic skin disorders. The invention thus also relates to the use of compounds of the formula I and their pharmacologically acceptable salts and N-oxides for the treatment of those individuals suffering from dermatoses.

The use of the compounds of the formula I particularly takes place in the form of those pharmaceuticals suitable for topical application. To prepare the pharmaceuticals, the compounds of the formula I and/or their pharmacologically acceptable salts and/or their N-oxides (=active substances) are preferably mixed with suitable pharmaceutical auxiliaries and further processed to suitable medicinal formulations. Examples of suitable medicinal formulations which may be mentioned are powders, emulsions, suspensions, sprays, oils, ointments, fatty ointments, creams, pastes, gels or solutions, in which the content of active substance is advantageously between 0.1 and 99%.

The person skilled in the art is aware, on the basis of his expert knowledge, of which auxiliaries are suitable for the desired medicinal formulations. Besides solvents, gel formers, ointment bases and other active substance vehicles it is possible to use, for example, antioxidants, dispersants, emulsifiers, preservatives, solubilizers or permeation promoters.

In addition, the 3-amino-6-arylpyridazines according to the invention, and their salts and N-oxides, are suitable for preventing and treating pathological states which are caused by certain cytokines (in particular by interleukins and, especially, by tumor necrosis factor) as well as leukotrienes, in which connection treatment of septic shock and of the toxic shock syndrome is particularly emphasized.

The 3-amino-6-arylpyridazines according to the invention, and their salts and N-oxides, can furthermore be used to prevent and treat allergic and/or chronic false reactions in the region of the upper respiratory tract (pharyngeal space, nose) and the adjoining regions (paranasal sinuses, eye) such as, for example, allergic rhinitis/sinusitis, chronic rhinitis/sinusitis, allergic conjuctivitis and nasal polyps.

BIOLOGICAL INVESTIGATIONS

The investigated compounds are identified in the following tables by numbers which are assigned as follows:

1. 3-amino-6-(3-methoxy-4-propoxyphenyl)pyridazine
2. 3-amino-6-[4-methoxy-3-(2-methylpropoxy)phenyl]pyridazine
3. 3-amino-6-[4-methoxy-3-(1-methylethoxy)phenyl]pyridazine
4. 3-amino-6-[3-methoxy-4-(2-methylpropoxy)phenyl]pyridazine
5. 3-amino-6-[3-methoxy-4-(1-methylethoxy)phenyl]pyridazine
6. 3-amino-6-(3-cyclopentyloxy-4methoxyphenyl)pyridazine
7. 3-amino-6-(3-cyclohexyloxy-4-methoxyphenyl)pyridazine
8. 3-amino-6-(3-cycloheptyloxy-4-methoxyphenyl)pyridazine
9. 3-amino-6-[4-ethoxy-3-(2-methylpropoxy)phenyl]pyridazine
10. 3-amino-6-(4-difluoromethoxy-3-ethoxyphenyl)pyridazine
11. 3-amino-6-(4-difluoromethoxy-3-methoxyphenyl)pyridazine
12. 3-amino-6-(3-difluoromethoxy-4-ethoxyphenyl)pyridazine
13. 3-amino-6-(3-cyclobutylmethoxy-4-methoxyphenyl)pyridazine
14. 3-amino-6-(3-cyclopentyloxy-4-difluoromethoxyphenyl)pyridazine
15. 3-amino-6-[4-difluoromethoxy-3-(1-methylethoxy)phenyl]pyridazine
16. 3-amino-6-[4-difluoromethoxy-3-(2,2,2-trifluoroethoxy)pyridazine
17. 3-amino-6-[4-difluoromethoxy-3-(2-methylpropoxy)phenyl]pyridazine
18. 3-amino-6-(3-cyclopropylmethoxy-4-difluoromethoxyphenyl)pyridazine
19. 3-amino-6-(4-difluoromethoxy-3-ethoxyphenyl)pyridazine 2-oxide
20. 3-amino-6-(4-difluoromethoxy-3-methoxyphenyl)pyridazine 2-oxide
21. 3-amino-6-(3-difluoromethoxy-4-ethoxyphenyl)pyridazine 2-oxide
22. 3-amino-6-[4-difluoromethoxy-3-(1-methylethoxy)phenyl]pyridazine 2-oxide
23. 3-amino-6-[4-difluoromethoxy-3-(2-methylpropoxy)phenyl]pyridazine 2-oxide
24. 3-amino-6-(3-cyclopentyloxy-4-difluoromethoxyphenyl)pyridazine 2-oxide
25. 3-amino-6-[4-difluoromethoxy-3-(2,2,2-trifluoroethoxy)phenyl]pyridazine 2-oxide
26. 3-amino-6-(3-cyclopropylmethoxy-4-difluoromethoxyphenyl]pyridazine 2-oxide The bronchospasmolytic effect of the compounds on the chain of tracheal rings from guinea pigs was tested in vitro as follows:

four parallel chains of tracheal rings, each consisting of 6 single rings, from guinea pigs (female and male, 430–600 g) in an organ bath [5 ml, Krebs-Henseleit solution with added phentolamine ($10^{-5}$ mol/l), 37° C., initial tension of the organs 2 g, aeration with 5% $CO_2$/95% $O_2$] develop a stable tonic spontaneous contracture after about 20 to 30 minutes. Relaxation of these permanently contracted organs can be brought about under isometric measurement conditions by administration of the test substance in a concentration which increases cumulatively in half logarithms (for example $1\times10^{-6}+2\times10^{-6}+7\times10^{-6}2\times10^{-5}$ etc. mol/l), with a constant relaxation response being awaited after each single dose of the test substance before the next higher concentration is administered. Thus, a complete dose-effect plot for the test substance is obtained over a period of 20 to 30 minutes. The particular relaxation is expressed as a percentage fraction of the maximum relaxation achievable by administration of (—)isoprenaline ($10^{-6}$ mol/l). The measure used for the bronchodilator activity is the concentration of the test substance which brings about 50% of the maximum achievable relaxation expressed by the negative logarithm of the $EC_{50}$ mol/l: $-lg[EC_{50}]$.

The values of $-lg[EC_{50}]$ and the ratios of the $EC_{50}$ values for theophylline and the investigated substance are indicated in Table 1. The values which were found show that the compounds according to the invention are very superior to theophylline in respect of the bronchospasmolytic activity.

TABLE 1

| Serial No. | $-lg[EC_{50}]$ | $[EC_{50}]$ theophylline/ $[EC_{50}]$ substance |
|---|---|---|
| 6 | 5.18 | 20.4 |
| 7 | 5.03 | 14.5 |
| 8 | 5.39 | 33.2 |
| 9 | 5.01 | 13.8 |
| 10 | 5.08 | 16.2 |
| 11 | 5.31 | 27.6 |
| 12 | 5.35 | 30.2 |
| 14 | 5.18 | 20.4 |
| 19 | 6.82 | 893 |
| 20 | 6.35 | 302 |
| 21 | 6.25 | 240 |
| 22 | 5.52 | 44.7 |
| 23 | 5.52 | 44.7 |
| 24 | 5.69 | 65.5 |
| 25 | 6.45 | 380 |
| 26 | 6.00 | 135 |
| Theophylline | 3.87 | 1.0 |

The bronchospasmolytic effect was also determined in the "histamine-induced bronchospasm in anesthetized guinea pigs" model:

In this model, pharmacodynamic and toxic effects on internal sensitive receptors, on respiration and on the cardiovascular system of guinea pigs are recorded simultaneously [U. Kilian, E. Müller, E. Ch. Dittmann and J. Hamacher, Arzneimittel-Forschung 28 (II) 1699–1708, 1978]. The pneumotachogram of anesthetized (ethylurethane 1.25 g/kg i.p.) monovagotomized, spontaneously breathing guinea pigs (male, 350–450 g) was recorded and, to characterize the bronchospasm induced by histamine (0.09–0.18 μmol/kg i.v.), the maximum rate of flow of the respiratory air was measured during expiration ($Vmax_e$).

One histamine spasm before administration of the substance was compared with several histamine spasms after administration of the substance. The test substances were administered intravenously (i.v.) and/or intrajejunally (i.j.).

It was found that the investigated compounds inhibit the histamine-induced bronchospasm in anesthetized guinea pigs about 2–5 times more than does theophylline.

TABLE 2

Average percentage bronchospasmolytic effect 0–1 h after administration and percentage bronchospasmolytic effect after 1 h after administration, measured by the inhibition of the histamine-induced decrease in Vmax.

| Serial No. | Dose μmol/kg | % inhibition (0–1 h) i.v. | % inhibition (0–1 h) i.j. admin. | % inhibition after 1 h i.v. | % inhibition after 1 h i.j. admin. |
|---|---|---|---|---|---|
| 3 | 20 | 34 | | 20 | |
| 6 | 20 | 22 | | is | |
| 9 | 20 | 16 | | 20 | |
| 10 | 20 | 38 | | 44 | |
| 11 | 20 | 30 | | 26 | |
| 18 | 20 | 31 | | 35 | |
| | 10 | 33 | 32 | 38 | 43 |
| | 5 | 40 | | 49 | |
| 19 | 20 | 71 | | 81 | |
| 20 | 20 | 40 | | 48 | |
| 25 | 20 | 34 | | 33 | |
| 26 | 20 | 15 | | 12 | |
| Theophylline | 100 | 34 | 45 | 22 | 44 |
| | 60 | 25 | 37 | 12 | 42 |
| | 20 | 13 | 11 | 5 | 8 |

In addition, the bronchospasmolytic effect was tested on the "protective effect against acetylcholine-induced bronchospasm in conscious guinea pigs" model:

The test procedure is based on T. Olsson, Acta Allergologica 26, 438–447 (1971). Guinea pigs (250–350 g) are exposed in a closed Plexiglass cylinder (volume 5 ) to an acetylcholine mist (0.06% in 0.9% sodium chloride solution; Heyer Use 77 ultrasonic atomizer) before administration of the substance and twice at an interval of 20 minutes after administration of the substance. The time from the start of atomization to the onset of marked breathing difficulties (in some cases hypoxic convulsion in the lateral position) is measured and called the latency time. An increase in the latency time after administration of the substance to at least three times the average latency time before administration of the substance is regarded as a protective effect, and the number of protected animals in the group is determined. The test substances are administered orally by stomach tube (dose 100 μmol/kg, volume 1 ml/kg, suspending agent 4% strength Methocel suspension in 0.9% strength sodium chloride solution).

In the control test (without administration of substance), the latency time is 2 minutes. The test substance is administered orally by stomach tube (standard dose 100 μmol, volume 1 ml of 4% strength Methocel suspension in 0.9% strength sodium chloride solution/kg). After 30 minutes, the animals are again exposed to the acetylcholine mist and the latency times are measured. An increase in the latency time to at least three times the length is regarded as a protective effect.

TABLE 3

Protective effect against acetylcholine-induced bronchospasm in concious guinea pigs determined 30 minutes after oral administration of substance or placebo. The percentage of protected animals compared with the control group is indicated.

| Serial No. | Dose μmol/kg | % protective effect |
|---|---|---|
| 2 | 30 | 50 |
| | 100 | 80 |
| 3 | 30 | 50 |
| | 100 | 70 |
| | 300 | 80 |
| 4 | 100 | 35 |
| 5 | 100 | 45 |
| 6 | 30 | 35 |
| | 100 | 85 |

TABLE 3 -continued

Protective effect against acetylcholine-induced bronchospasm in concious guinea pigs determined 30 minutes after oral administration of substance or placebo. The percentage of protected animals compared with the control group is indicated.

| Serial No. | Dose μmol/kg | % protective effect |
|---|---|---|
| 7 | 100 | 35 |
| 8 | 100 | 50 |
| 9 | 100 | 65 |
| 10 | 100 | 50 |
| 11 | 100 | 80 |
| 12 | 100 | 50 |
| 13 | 100 | 65 |
| 18 | 10 | 75 |
|  | 100 | 75 |
| 19 | 4 | 50 |
| 20 | 2 | 50 |
| 22 | 100 | 60 |
| 24 | 100 | 60 |
| 25 | 10 | 45 |
|  | 100 | 70 |
| 26 | 10 | 70 |
| Theophylline | 100 | 20 |
|  | 200 | 40 |
|  | 400 | 70 |

The specific inhibition of phosphodiesterase IV (PDE IV=high-affinity cAMP-PDE which cannot be inhibited by cGMP, rolipram-sensitive) is regarded as particularly indicative of an expected bronchospasmolytic and/or antiinflammatory effect. The specificity of the inhibition is moreover described by the ratio [IC$_{50}$]$_{PDE-III}$/[IC$_{50}$]$_{PDE-IV}$ (PDE III=high-affinity cAMP-PDE which can be inhibited by cGMP) [H. Hidaka et al., Adv. Cycl. Nucl. Res. 13, 145 (1984); TiPS 5, 237 (1984); R. Weishaar et al., J. Med. Chem. 28, (1985); S. A. Harrison et al., Molec. Pharmac. 29, 506 (1986); J. Klein-Tebbe et al., Allergologie 12, 12 (1989); C. Schudt et al., Allergologie 12, 12, (1989); C. Schudt et al., Agents and Action 1991 in press; C. D. Nicholson et al., TiPS 12, (1), 19 (1991)].

For this reason, the PDE inhibition by the compounds according to the invention was determined on a PDE III isolated from human platelets and on PDE IV isolated from human polymorphonuclear neutrophilic cells (PMNs) and from the dog trachea. Phosphodiesterases III and IV are isolated by chromatography as described by Polson et al., Biochem. Pharmacol. 31, 3403-3406 (1982).

The substances are dissolved and diluted further in DMSO. 2.1 μl samples from a series of solutions diluted up to 100 fold are mixed with 212 μl of reaction mixture. The reaction mixture contains Hepes (100 mmol/l), DTE (5 mmol/l), MgCl$_2$ (5 mmol/l), CaCl$_2$ (10 μmol/l), BSA fraction V 0.5 mg, ml, cAMP 0.5 μmol/l, 2,8-$^3$H-cAMP 250,000 cpm/ml (0.3 μCi/ml, S.A. 33.5 μCi/mmol), SV (snake venom) 25 μg/212 μl of test mixture.

Table 4 lists the negative logarithms of the IC$_{50}$ values found and the ratios of the IC$_{50}$ values for the inhibition of PDE III and PDE IV found for the substances according to the invention. The substances according to the invention inhibit PDE IV significantly more specifically and strongly than does theophylline.

TABLE 4

| | Inhibition of PDE III and PDE IV | | | | |
|---|---|---|---|---|---|
| Serial No. | PDE III hum. platelets −1 g[IC$_{50}$] | PDE IV dog trachea −1 g[IC$_{50}$] | PDE IV hum. PMNs −1 g[IC$_{50}$] | [IC$_{50}$] PDE III/ [IC$_{50}$] PDE IV dog tr. | [IC$_{50}$] PDE III/ [IC$_{50}$] PDE IV PMNs |
| 2 | 3.68 | <5.0 | | <20.9 | |
| 3 | 3.66 | 5.30 | | 43.7 | |
| 6 | <4.0 | 6.48 | 6.18 | >304 | >151 |
| 7 | 4.22 | 5.17 | | 8.9 | |
| 8 | 4.11 | 5.37 | | 18.2 | |
| 9 | 3.90 | 5.68 | | 60.2 | |
| 10 | 3.65 | 5.37 | | 52.5 | |
| 11 | 3,71 | 5.09 | | 22.9 | |
| 12 | 3.50 | 4.42 | | 9.6 | |
| 13 | 3.65 | 4.88 | | 17.0 | |
| 14 | 4.27 | | 7.15 | | 1466 |
| 15 | 3.97 | | 6.78 | | 794 |
| 16 | 3.48 | | 6.88 | | 2515 |
| 17 | 3.82 | | 6,96 | | 1466 |
| 18 | 3.84 | | 7.47 | | 4265 |
| 19 | 4.20 | 5.82 | 6.58 | 41.7 | 240 |
| 20 | 4.83 | 5.08 | 5.89 | 1.8 | 11.5 |
| 21 | 4.35 | — | 5.19 | — | 6.9 |
| 22 | 4.92 | — | 6.26 | — | 21.9 |
| 23 | 3.90 | — | 7.03 | — | 1350 |
| 24 | 4.32 | — | 7.24 | — | 832 |
| 25 | 4.15 | — | 6.42 | — | 186 |
| 26 | 4.74 | — | 7.48 | — | 550 |
| Theophylline | 3.82 | — | 3.77 | | 0.3 |

We claim:

1. A 3-Amino-6-arylpyridazine of the formula I

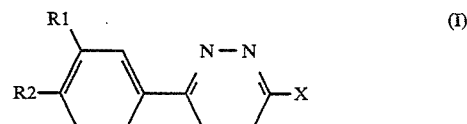

in which one of the substituents R1 and R2 denotes methoxy, difluoromethoxy or ethoxy and the other denotes 1-5C-alkoxy, 4-7C-cycloalkoxy, 3-7C-cycloalkylmethoxy, 3-5C-alkenyloxy or 1-4C-polyfluoroalkoxy, X denotes amino or a salt with acid or an N-oxide thereof.

2. A 3-Amino-6-arylpyridazine of the formula I according to claim 1, in which
R1 denotes methoxy, difluoromethoxy or ethoxy,
R2 denotes 1-4C-alkoxy, 4-7C-cycloalkoxy, 3-6C-cycloalkylmethoxy, 3-4C-alkenyloxy or 1-2C-polyfluoroalkoxy and
X denotes amino,
or a salt with acid or an N-oxide thereof.

3. A 3-Amino-6-arylpyridazine of the formula I according to claim 1, in which
R1 denotes 3-4C-alkoxy, 4-7C-cycloalkoxy, 3-6C-cycloalkylmethoxy, 3-4C-alkenyloxy or 1-2C-polyfluoroalkoxy,
R2 denotes methoxy, difluoromethoxy or ethoxy and
X denotes amino, or a salt with acid or an N-oxide thereof.

4. A compound of formula I according to claim 1, in which one of the substituents R1 and R2 denotes methoxy, difluoromethoxy or ethoxy and the other denotes 1-4C-alkoxy, 4-7C-cycloalkoxy, 3-6C-cycloalkylmethoxy or 1-2C-polyfluoroalkoxy, and X denotes amino, or a salt with acid or an N-oxide thereof.

5. A compound of formula I according to claim 1, in which R1 denotes 2-4C-alkoxy, cyclopentyloxy, cyclopropylmethoxy, cyclobutylmethoxy, difluoromethoxy or 2,2,2-trifluoroethoxy, R2 denotes methoxy, ethoxy or difluoromethoxy, and X denotes amino, or a pharmacologically acceptable salt with acid or an N-oxide thereof.

6. A pharmaceutical composition comprising an effective amount of a compound of claim 1, a pharmacologically-acceptable salt thereof with an acid or an N-oxide thereof, and a pharmacologically-acceptable carrier.

7. A method for achieving an effect in a mammal which comprises administering an effective amount of a compound of claim 1, of a pharmacologically-acceptable salt thereof with an acid or of an N-oxide thereof to the mammal, wherein the effect is treatment or prophylaxis of a disorder of the bronchi.

8. A method of claim 7 wherein the mammal is a human.

* * * * *